United States Patent
Perlov et al.

(10) Patent No.: US 7,504,066 B2
(45) Date of Patent: Mar. 17, 2009

(54) OZONE PLASMA MEDICAL STERILIZATION

(75) Inventors: Gena Perlov, Haifa (IL); Boris Malkin, Haifa (IL); Shmuel Yannai, Haifa (IL)

(73) Assignee: Tuttnauer Israel Ltd., Jerusalem (IL)

( * ) Notice: Subject to any disclaimer, the term of this patent is extended or adjusted under 35 U.S.C. 154(b) by 554 days.

(21) Appl. No.: 10/659,354

(22) Filed: Sep. 11, 2003

(65) Prior Publication Data

US 2005/0058569 A1    Mar. 17, 2005

(51) Int. Cl.
    *A61L 2/14*      (2006.01)
(52) U.S. Cl. .............................. 422/23; 422/27; 422/33; 422/186.23; 422/292
(58) Field of Classification Search ............... 422/1, 422/3, 22, 23, 186.07, 186.23; 250/455.11
See application file for complete search history.

(56) References Cited

U.S. PATENT DOCUMENTS

| | | | | |
|---|---|---|---|---|
| 4,348,357 A | * | 9/1982 | Bithell | 422/22 |
| 5,120,512 A | * | 6/1992 | Masuda | 422/297 |
| 5,302,343 A | * | 4/1994 | Jacob | 422/23 |
| 5,868,999 A | * | 2/1999 | Karlson | 422/30 |
| 2003/0133832 A1 | * | 7/2003 | D'Ottone | 422/29 |
| 2004/0022673 A1 | * | 2/2004 | Protic | 422/28 |

FOREIGN PATENT DOCUMENTS

WO    WO9835708 A1 * 8/1998

OTHER PUBLICATIONS

Chollet et al., WO 98/35708, Aug. 20, 1998, machine translation.*

* cited by examiner

*Primary Examiner*—Elizabeth L McKane
(74) *Attorney, Agent, or Firm*—Mark M. Friedman

(57) ABSTRACT

A method for sterilizing at least one item in a chamber, comprising the steps of: disposing the at least one item in the chamber; pumping the atmosphere from the chamber until the atmosphere of the chamber has a pressure of less than ten torr; adding water vapor and ozone to the chamber; and generating electrical discharge in the chamber, such that the electrical discharge produces OH radicals from the water vapor and the ozone so as to contribute to sterilization of at least part of the at least one item.

28 Claims, 9 Drawing Sheets

OZONE PLASMA MEDICAL STERILIZATION

FIELD AND BACKGROUND OF THE INVENTION

The present invention relates to sterilization of medical equipment and, in particular, it concerns sterilization of medical equipment using ozone plasma.

Of most relevance to the present invention is the STERRAD® 100S Sterilization System commercially available from Johnson & Johnson Company. The STERRAD® System is based on the generation of low-temperature gas plasma from hydrogen peroxide. The low temperature gas plasma includes OH radicals which perform the sterilization of the medical equipment. The system does not leave toxic residues on surgical instruments and equipment, eliminating the need for a lengthy aeration phase, and sterile instruments may be used immediately following the 55-minute sterilization cycle. A shortcoming of the aforementioned system is due to the need to use hydrogen peroxide. First, hydrogen peroxide is expensive. Second, hydrogen peroxide needs to be treated carefully. Third, a supply of hydrogen peroxide needs to be purchased specially to operate the system.

There is therefore a need for an effective sterilization system and method for medical equipment using cheap and readily available supplies.

SUMMARY OF THE INVENTION

The present invention is an ozone-plasma medical sterilization system and method of operation thereof.

According to the teachings of the present invention there is provided, a method for sterilizing at least one item in a chamber, comprising the steps of: (a) disposing the at least one item in the chamber; (b) pumping the atmosphere from the chamber until the atmosphere of the chamber has a pressure of less than one torr; (c) adding water vapor and ozone to the chamber; (d) and generating electrical discharge in the chamber, such that the electrical discharge produces OH radicals from the water vapor and the ozone so as to contribute to sterilization of at least part of the at least one item.

According to a further feature of the present invention, the step of pumping is performed by pumping the atmosphere from the chamber until the atmosphere of the chamber has a pressure of less than half a torr.

According to a further feature of the present invention, there is also provided the step of producing the ozone from oxygen using an ozonizer.

According to a further feature of the present invention, there is also provided the step of producing the water vapor by passing at least part of the ozone over a reservoir of water.

According to a further feature of the present invention, the step of adding is performed, such that the adding increases the pressure of the atmosphere within the chamber.

According to a further feature of the present invention, there is also provided the step of breaking the electrical discharge when the pressure of the atmosphere within the chamber is between 5 torr and 15 torr.

According to a further feature of the present invention, the step of adding is performed, such that the adding increases the pressure of the atmosphere within the chamber at least until the step of breaking is performed.

According to a further feature of the present invention, there is also provided the step of performing a cycle including the steps of pumping, adding, generating and breaking.

According to a further feature of the present invention, the step of performing the cycle is performed at least 20 times.

According to a further feature of the present invention, the step of performing the cycle is performed at least 60 times.

According to a further feature of the present invention, there is also provided the step of allowing the OH radicals to diffuse in the chamber for a specified diffusion time at the higher pressure end of the cycle.

According to a further feature of the present invention, there is also provided the step of recycling at least part of the ozone which was added to the chamber.

According to a further feature of the present invention, there is also provided the step of injecting radicals into the chamber.

According to a further feature of the present invention, the radicals include OH radicals.

According to a further feature of the present invention, the at least one item has an internal volume and the step of injecting is performed by injecting at least part of the radicals into the internal volume of the at least one item.

According to the teachings of the present invention there is also provided a method for sterilizing at least one item in a chamber using a plasma gun, comprising the steps of: (a) disposing the at least one item in the chamber; and (b) injecting radicals into the chamber so as to contribute to sterilization of at least part of the at least one item.

According to a further feature of the present invention, the radicals include OH radicals.

According to a further feature of the present invention, the at least one item has an internal volume and the step of injecting is performed by injecting at least part of the radicals into the internal volume.

According to a further feature of the present invention, there is also provided the step of mechanically connecting the at least one item to a connector arrangement, wherein the step of injecting is performed by injecting the part of the radicals into the internal volume via the connector arrangement.

According to the teachings of the present invention there is also provided a system for sterilizing at least one item, comprising: (a) a chamber having a first door, the first door being configured, such that the at least one item is entered into the chamber via the first door; (b) a pumping system associated with the chamber, the pumping system being configured to pump the atmosphere from the chamber until the atmosphere of the chamber has a pressure of less than one a torr; an ozone and water vapor system associated with the chamber, the ozone and water vapor system being configured for adding ozone and water vapor to the chamber; (c) an electrode arrangement disposed in the chamber; and (d) an electrical supply system electrically connected to the electrode arrangement, the electrical supply system and the electrode arrangement being configured for generating electrical discharge in the chamber, such that the electrical discharge produces OH radicals from the water and the ozone so as to contribute to sterilization of at least part of the at least one item.

According to a further feature of the present invention, the pumping system is configured to pump the atmosphere from the chamber until the atmosphere of the chamber has a pressure of less than half a torr.

According to a further feature of the present invention, the ozone and water vapor system includes an ozonizer configured to produce the ozone from oxygen.

According to a further feature of the present invention, the ozone and water vapor system includes a reservoir configured for storing water, the ozone and water vapor system being configured to produce the water vapor by passing at least part of the ozone over the water.

According to a further feature of the present invention, there is also provided a control system configured for actuating the ozone and water vapor system, such that the ozone and water vapor system adds the ozone and the water vapor to the chamber thereby increasing the pressure of the atmosphere of the chamber at least until the electrical discharge is broken.

According to a further feature of the present invention, the control system is configured for performing a cycle including: (a) actuating the pumping system to pump the atmosphere of the chamber until the atmosphere of the chamber has a pressure of less than half a torr; (b) actuating the electrical supply system to generate the electrical discharge in the chamber; (c) actuating the ozone and water vapor system, such that the ozone and water vapor system adds ozone and water vapor to the chamber thereby increasing the pressure of the atmosphere within the chamber; and (d) actuating the electrical supply system to break the electrical discharge when the pressure of the atmosphere within the chamber is between 5 and 15 torr.

According to a further feature of the present invention, the control system is configured for performing the cycle at least 20 times.

According to a further feature of the present invention, the control system is configured for performing the cycle at least 60 times.

According to a further feature of the present invention, there is also provided a biological filter configured to filter air entering the chamber on completion of a sterilization process.

According to a further feature of the present invention, there is also provided a ozone destruction filter configured to substantially prevent a part of the ozone exiting to a surrounding atmosphere when the pumping system is actuated.

According to a further feature of the present invention, the electrode arrangement includes an electrode which is implemented as at least part of the first door.

According to a further feature of the present invention, there is also provided a second door configured, such that the at least one item is removed from the chamber via the second door on completion of a sterilization process.

According to a further feature of the present invention, the electrode arrangement includes a first electrode which is implemented as at least part of the second door.

According to a further feature of the present invention, the electrode arrangement includes a second electrode which is implemented as at least part of the first door.

According to a further feature of the present invention the electrode arrangement includes a third electrode and a fourth electrode and the electrode arrangement and the electrical supply system are configured, such that when the electrical supply system is actuated there is at least one central region of zero field gradient within the chamber.

According to a further feature of the present invention, there is also provided a secondary pumping system associated with the chamber, the secondary pumping system being configured to recycle at least part of the ozone which was added to the chamber.

According to a further feature of the present invention, there is also provided a plasma gun configured for injecting radicals into the chamber.

According to a further feature of the present invention, the radicals include OH radicals.

According to a further feature of the present invention, there is also provided a connector arrangement configured, such that the plasma gun injects at least part of the radicals into an internal volume of the at least one item.

According to the teachings of the present invention there is also provided a plasma gun system, comprising: (a) a housing; (b) a supply system associated with the housing, the supply system being configured to produce first ions and second ions in the housing, the first ions having a first polarity, the second ions having a second polarity; (c) a vacuum pump associated with the housing; and (d) a first arrangement configured for being charged with the first polarity in order to: (i) repel the first ions, such that at least 50% of the first ions are removed from the housing via the vacuum pump; and (ii) neutralize at least 50% of the second ions, thereby producing radicals.

According to a further feature of the present invention, there is also provided a second arrangement configured for being charged with the second polarity in order to repel remaining the second ions, such that at least 50% of the remaining second ions are removed from the housing via the vacuum pump.

According to a further feature of the present invention, there is also provided a dispersing arrangement configured to disperse the first ions and the second ions in order to reduce recombination of the first ions and the second ions.

According to a further feature of the present invention, the dispersing arrangement includes: (a) a conducting arrangement; (b) an insulation layer configured to insulate the conducting arrangement from the first ions and the second ions; and (c) an alternating power supply electrically connected to the conducting arrangement.

According to a further feature of the present invention, the conducting arrangement includes two cross-aligned grills.

According to a further feature of the present invention, the first arrangement includes a mesh.

According to a further feature of the present invention, the supply system includes: (a) a water vapor supply configured to produce water vapor in the supply system; (b) an electrode arrangement disposed in the supply system; and (c) a power supply electrically connected to the electrode arrangement, the power supply and the electrode arrangement being configured for generating electrical discharge in the supply system, such that the electrical discharge produces OH ions from the water vapor, wherein the radicals include OH radicals.

According to a further feature of the present invention, there is also provided a dry vacuum pump configured for pumping the radicals from the housing.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an ozone-plasma medical sterilization system and method of operation thereof.

The principles and operation of an ozone-plasma medical sterilization system according to the present invention may be better understood with reference to the drawings and the accompanying description.

By way of introduction, the system and method of the present invention generates electrical discharge in chamber containing plasma of ozone and water vapor to produce OH radicals for sterilizing. The chemical reaction is given by the following equation:

$$2O_3 \text{ (Ozone)} + 3H_2O \text{ (water vapor)} = 6OH \quad \text{(equation 1)}.$$

Figure 1:
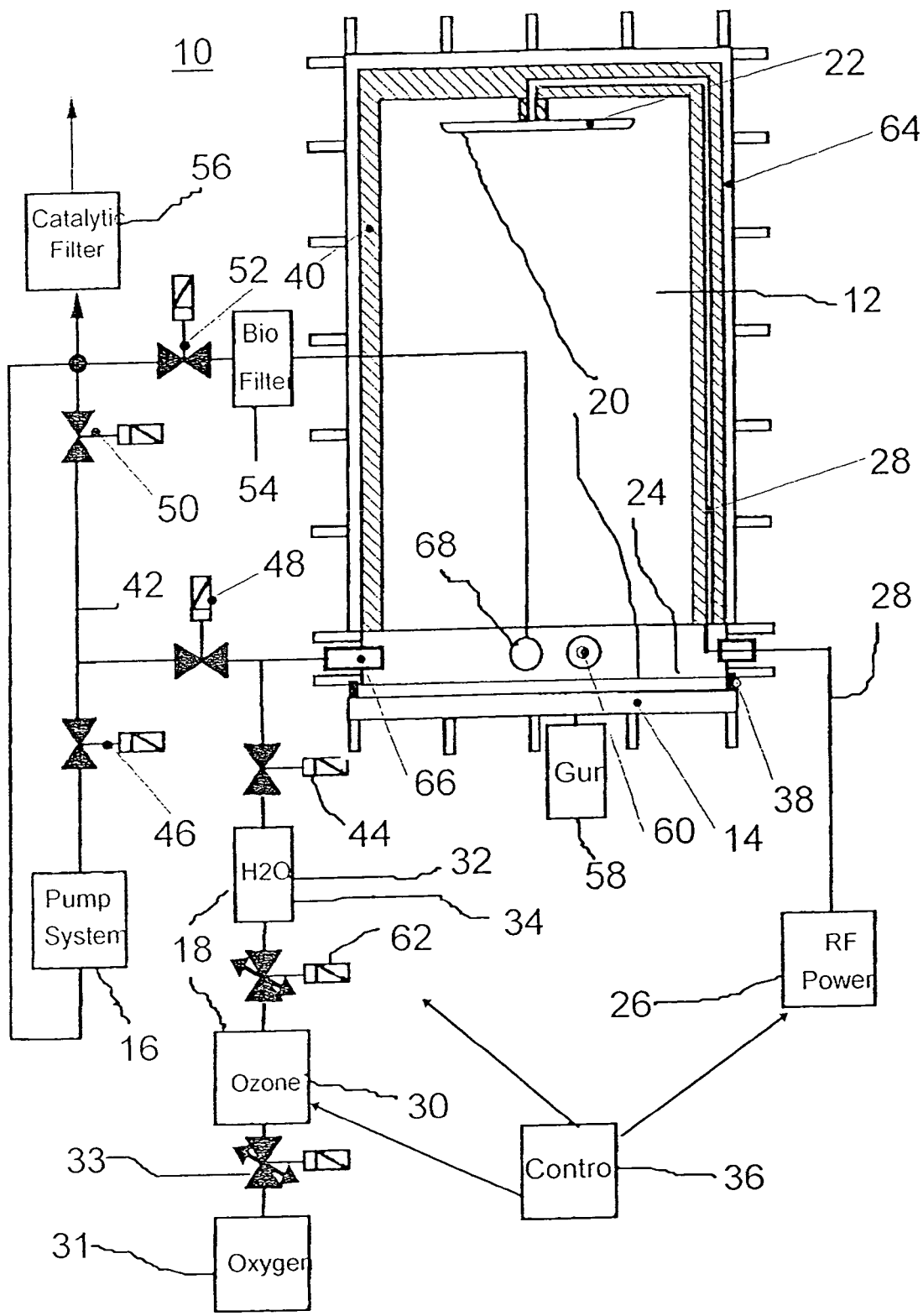
FIG. 1 is a schematic diagram of an ozone-plasma sterilization system that is constructed and operable in accordance with a preferred embodiment of the present invention.

Reference is now made to FIG. 1, which is a schematic diagram of an ozone-plasma sterilization system 10 that is constructed and operable in accordance with a preferred embodiment of the present invention. Sterilization system 10 includes a chamber 12 having a plurality of walls 64 and a door 14. Chamber 12 has a capacity of generally between 1 and 10,000 liters and preferably between 50 and 2,000 liters. Walls 64 are typically constructed from any material which withstands a vacuum. Door 14 is configured, such that one or more items for sterilization is entered into chamber 12 via door 14 in order to undergo sterilization. Door 14 includes a seal arrangement 38 configured to ensure that air does not enter or leave sterilization system 10 during operation. Seal arrangement 38 is typically formed from any material which withstands a vacuum, OH corrosion and plasma discharge conditions, for example, but not limited to, VITON which is commercially available from DuPont Dow Elastomers L.L.C., 300 Bellevue Parkway, Suite300, Wilmington, Del. 19809. Sterilization system 10 also includes a pumping system 16 associated with chamber 12. Pumping system 16 is configured to pump the atmosphere from chamber 12 until the atmosphere of chamber 12 has a pressure of generally less than 1 torr, preferably less than 0.5 torr. Pumping system 16 generally includes an inlet and outlet filter (not shown). Pumping system 16 includes one or more electronic pressure sensor arrangements disposed in chamber 12 for measuring the pressure of the atmosphere of chamber 12. The electronic pressure sensor arrangements are configured to sense pressures from approximately 0 to at least 760 torr. It will be appreciated by those ordinarily skilled in the art that at least one of the electronic pressure sensors needs to sense air pressure accurately in the range of approximately 0 to 20 torr. By way of example, pumping system 16 is generally configured to have a pumping rate of 80 cubic meters per hour when the volume of chamber 12 is 100 liters. Pumping system 16 is typically a dry vacuum pump, for example, but not limited to, pump E1M80 with foreline traps which is commercially available from BOC Edwards of 301 Ballardvale Street, One Edwards Park, Wilmington, Mass. 01887. Sterilization system 10 also includes an ozone and water vapor system 18 associated with chamber 12. Ozone and water vapor system 18 is configured for adding ozone and water vapor to chamber 12. Ozone and water vapor system 18 includes an ozonizer system 30 and an oxygen supply 31. Ozonizer system 30 is configured to produce ozone from oxygen supplied by oxygen supply 31. An adjustable valve 33 controls the supply of oxygen from oxygen supply 31 to ozonizer system 30. By way of example, ozonizer system 30 is generally configured to produce ozone at a rate of 200 grams per hour when chamber 12 has a capacity of 100 liters. A suitable ozonizer system 30 is commercially available from Ozontech Limited of Technion Hamama, PO Box 212, Nesher 36601, Israel. Ozone and water vapor system 18 includes a water vapor system 32. Water vapor system 32 includes a reservoir 34 configured for storing water. Ozone and water vapor system 18 is configured to produce water vapor by passing ozone produced by ozonizer system 30 over the surface of the water stored in reservoir 34. Ozone and water vapor system 18 is typically configured, such that the ozone and water vapor mixture entering chamber 12 has a humidity level of approximately 99%. In accordance with a most preferred embodiment of the present invention, reservoir 34 includes an ultrasonic device (not shown) which produces the water vapor. Sterilization system 10 also includes an electrode arrangement 20 disposed in chamber 12. Electrode arrangement 20 is typically formed from a non-magnetic material which withstands OH corrosion and plasma discharge conditions, for example, but not limited to, stainless steel. In accordance with this preferred embodiment electrode arrangement 20 includes two electrodes 22, 24. Electrode 24 is implemented as part of door 14. Sterilization system 10 includes an electrical supply system 26 electrically connected to electrode 22 of electrode arrangement 20 via a wire 28. Electrical supply system 26 is typically an AC plasma power supply, preferably in the radio frequency (RF) range, having a voltage output of between 400 and 2,000 volts and a power output of between 400 and 1250 watts. Electrode 24 is grounded. Chamber 12 includes an insulating layer 40 which prevents other surfaces of chamber 12 acting as electrodes. Insulating layer 40 is generally formed from, by way of example, but not limited to, PVDF, Teflon, Silicon or HDPE. Insulating layer 40 is not mechanically connected to chamber 12. Additionally, insulating layer 40 has a textured surface, which faces the walls of chamber 12. The textured surface enables air to enter between insulating layer 40 and the walls of chamber 12 in order to prevent insulating layer 40 collapsing inward when the pressure of the atmosphere of chamber 12 is reduced. The textured surface includes, by way of example, but not limited to, grooves with a depth and width of approximately 0.5 mm. Electrical supply system 26 and electrode arrangement 20 is configured for generating electrical discharge in chamber 12, such that the electrical discharge produces OH radicals from the water and ozone so as to contribute to sterilization of at least part of the one or more items for sterilization. Sterilization system 10 also includes a biological filter 54, for example, but not limited to, a High Efficiency Particulate Air (HEPA) Filter. Biological filter 54 is configured to filter air entering chamber 12 on completion of a sterilization process. Sterilization system 10 also includes an ozone destruction filter 56, typically a catalytic filter, configured to substantially prevent any ozone exiting to a surrounding atmosphere when pumping system 16 is actuated. The term "substantially prevent" is defined herein to include filtering ozone, such that only an acceptable level of ozone is allowed to exit sterilization system 10. The term "surrounding atmosphere" is defined herein to include the atmosphere external to sterilization system 10. Sterilization system 10 includes a tube network 42 and valves 44, 46, 48, 50, 52, 62. Tube network 42 and valves 44, 46, 48, 50, 52, 62 operationally connect together pumping system 16, ozone and water vapor system 18, biological filter 54 and ozone destruction filter 56. Tube network 42 is connected to chamber 12 via two openings 66, 68. Valves 44, 46, 48, 50, 52 are generally solenoid valves having two states, open or closed. Valve 62 is generally an adjustable solenoid valve configured to adjust the rate of flow of ozone leaving ozonizer system 30.

The method for producing OH radicals in chamber 12 is described in more detail with reference to FIGS. 2 and 3. The method described with reference to FIGS. 2 and 3 is performed using a control system 36 configured for actuating the components of sterilization system 10 described above, including valves 44, 46, 48, 50, 52.

Sterilization system 10 also includes a plasma gun 58 and a connector arrangement 60. Plasma gun 58 and connector arrangement 60 are configured for injecting OH radicals into the internal volume of one or more of the items for sterilization. Plasma gun 58 and connector arrangement 60 are described in more detail with reference to FIGS. 8 and 9, respectively.

Ozonizer system 30 is tested prior to use by actuating ozonizer system 30 to produce ozone which exists sterilization system 10 via valve 62, valve 44, valve 48, valve 50 and ozone destriction filter 56. Ozonizer system 30 includes an ozone sensor (not shown) for measuring the quantity of ozone being produced by ozonizer system 30 to ensure that ozonizer system 30 is operating at full capacity.

Figure 2:
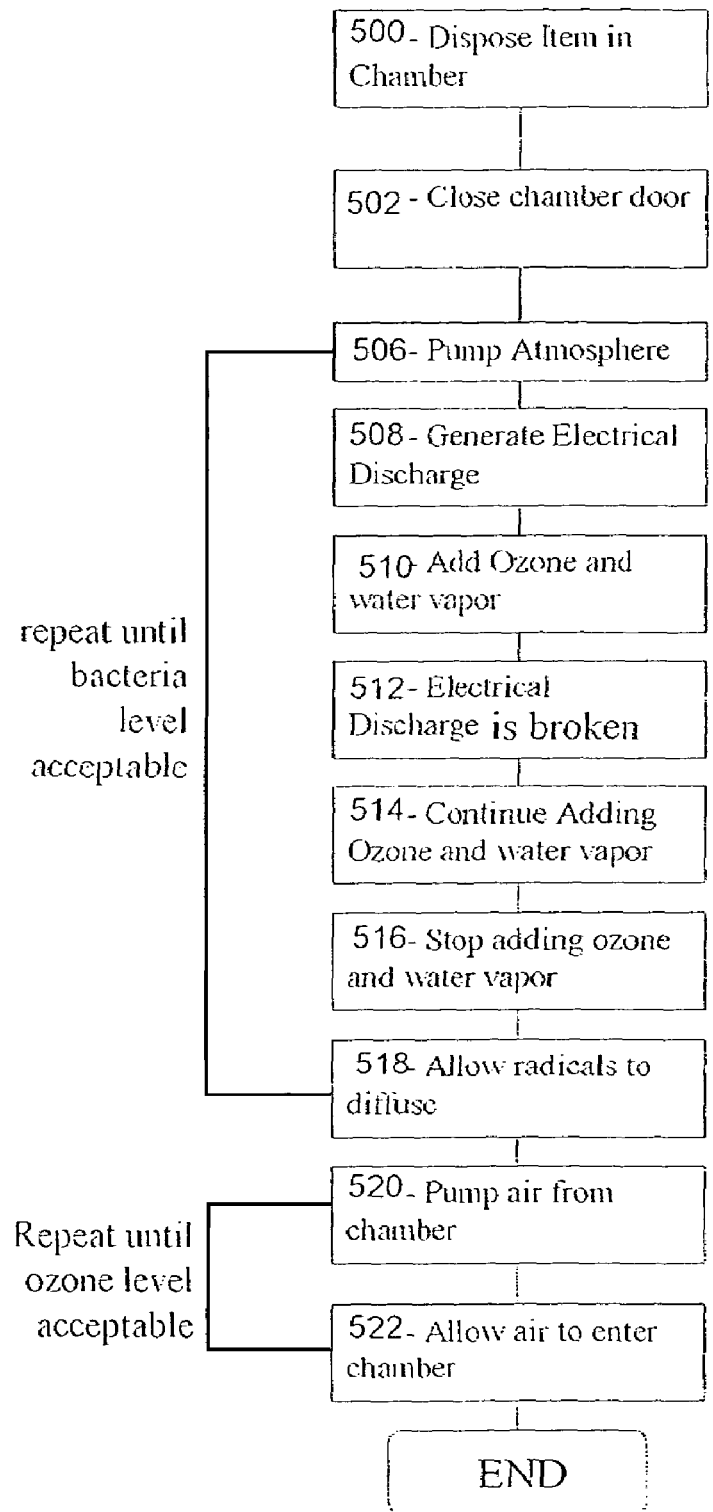
FIG. 2 is a flow chart showing the steps of a sterilization process using the sterilization system of FIG. 1.
Figure 3:
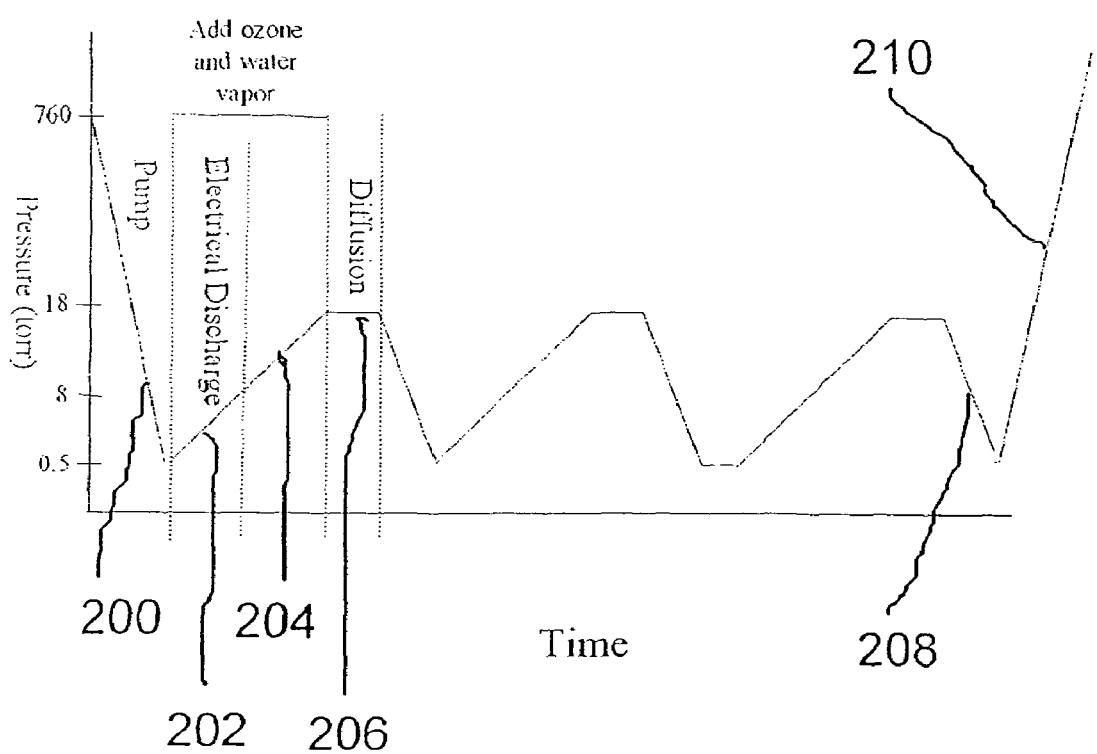
FIG. 3 is a graph of pressure (within the chamber of the sterilization system of FIG. 1) against time for the sterilization process of FIG. 2.

Reference is now made to FIGS. 2 and 3. FIG. 2 is a flow chart showing the steps of a sterilization process using sterilization system 10. FIG. 3 is a graph of pressure (within chamber 12 of sterilization system 10) against time for the sterilization process of FIG. 2. Reference is also made to FIG. 1. The sterilization process using sterilization system 10 includes the following steps. First, the items for sterilization are disposed in chamber 12 (block 500). Second, door 14 of chamber 12 is closed (block 502). Sterilization system 10 then performs a number of sterilization cycles, typically between 20 and 80 cycles, preferably 60 cycles, as follows. First, control system 36 opens valves 46, 48 and closes valves 44, 50, 52. Then control system 36 actuates pumping system 16 to pump the atmosphere of chamber 12 until the atmosphere of chamber 12 has a pressure typically in the range of 0.5 to 5 torr (block 506, line 200). Next, control system 36 closes valves 46, 48. Then control system 36 actuates electrical supply system 26 to generate electrical discharge in chamber 12 (block 508). Next, control system 36 opens valve 44. Then control system 36 actuates ozone and water vapor system 18, such that ozone and water vapor is "added" to chamber 12 thereby increasing the pressure of the atmosphere of chamber 12 (block 510) "at least" until control system 36 actuates electrical supply system 26 to break the electrical discharge (block 512, line 202). The electrical discharge is typically sustained for about 5 to 10 seconds and is typically broken when the pressure of the atmosphere in chamber 12 is generally in the range of 5 to 15 torr, preferably in the range of 7 to 10 torr. The electrical discharge is broken before the electrical discharge starts to cause damage to sterilization system 10 or any of the items for sterilization. The terms "added" "at least" are defined herein to include adding ozone and water vapor after the electrical discharge has been broken, typically until the pressure of the atmosphere within chamber 12 is between 15 and 20 torr (block 514, line 204). In each cycle, water vapor and ozone are generally added for a period of between 10 and 20 seconds. It should be noted that, optionally, adding ozone and water vapor to chamber 12 is commenced before the electrical discharge is generated. While the electrical discharge is sustained, the electrical discharge produces OH radicals from the water vapor and the ozone so as to contribute to sterilization of at least part of the one or more items for sterilization. The term "produces OH radicals from the water vapor and the ozone" is defined herein as, producing OH radicals from at least part of the water vapor and at least part of the ozone. It should be noted that even though the ozone and water vapor added after the electrical discharge has been broken are unlikely to produce a significant amount of OH radicals, the ozone and water vapor has a sterilization effect by itself. Then control system 36 terminates actuation of ozone and water vapor system 18 and closes valve 44 (block 516). Optionally, control system 36 allows a diffusion period between cycles thereby allowing the OH radicals to diffuse among the items for sterilization in chamber 12 for a specified diffusion time at the higher pressure end of each cycle (block 518, line 206). The diffusion period for each cycle is generally up to 10 minutes. The steps of blocks 506 to 518 are repeated until the bacteria on the items for sterilization is substantially eradicated, between 20 and 60 cycles depending upon the duration of the steps. After the final cycle, control system 36 opens valves 46, 48. Then control system 36 actuates pumping system 16 to pump the atmosphere from chamber 12 out of sterilization system 10 via ozone destruction filter 56 (block 520, line 208). Control system 36 then closes valves 46, 48 and opens valve 52 to allow air from the surrounding atmosphere to enter chamber 12 via ozone destruction filter 56 and biological filter 54 (block 522, line 210). The steps of blocks 520 and 522 are repeated until the ozone remaining in chamber 12 is below an acceptable level, typically 0.1 parts per million, before allowing door 14 to be opened. An ozone meter (not shown) measures the level of ozone leaving chamber 12 via biological filter 54. Door 14 has a safety lock (not shown) which is controlled by control system 36 to prevent door 14 being opened when the ozone level in chamber 12 is too high.

Figure 4:
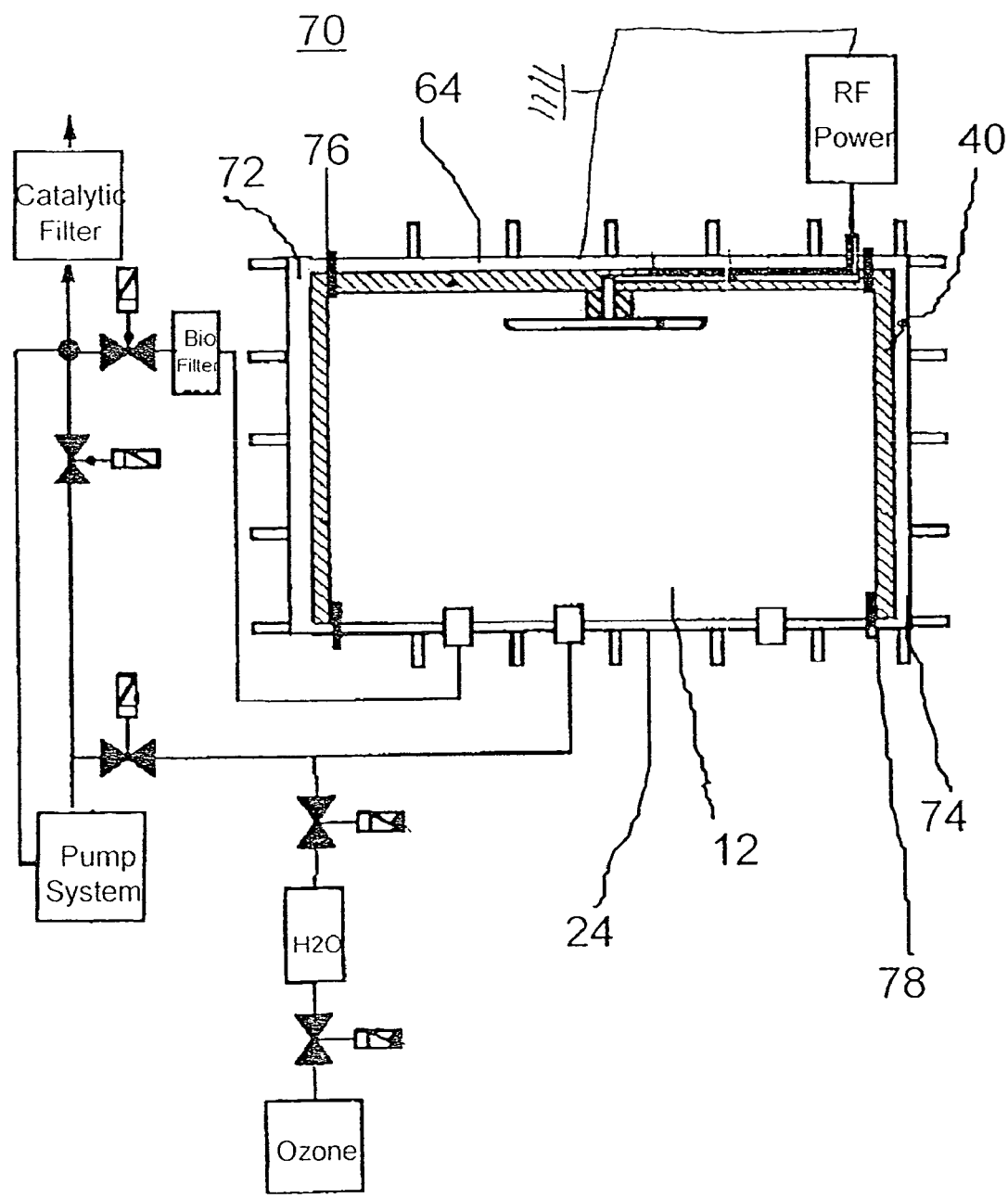
FIG. 4 is a schematic diagram of an ozone-plasma sterilization system that is constructed and operable in accordance with a first alternate embodiment of the present invention.

Reference is now made to FIG. 4, which is a schematic diagram of an ozone-plasma sterilization system 70 that is constructed and operable in accordance with a first alternate embodiment of the present invention. Ozone-plasma sterilization system 70 is the same as sterilization system 10 (FIG. 1) except for the following differences. Ozone-plasma sterilization system 70 includes two doors 72, 74. Door 72 is configured, such that one or more items for sterilization is entered into chamber 12 via door 72 in order to undergo sterilization. Door 74 is configured, such that the sterilized items are removed from chamber 12 via door 74 on completion of the sterilization process. Doors 72, 74 include two seal arrangements 76, 78, respectively, configured to ensure that air does not enter or leave sterilization system 10 during operation. Electrode 24 is not implemented as part of doors 72, 74. Electrode 24 is implemented as part of walls 64 of chamber 12. Electrode 24 is grounded. Therefore, the surfaces of doors 72, 74 facing into chamber 12 are insulated by insulating layer 40. All surfaces of walls 64 facing into chamber 12 are insulated with insulating layer 40 except for the region of electrode 24.

Figure 5:
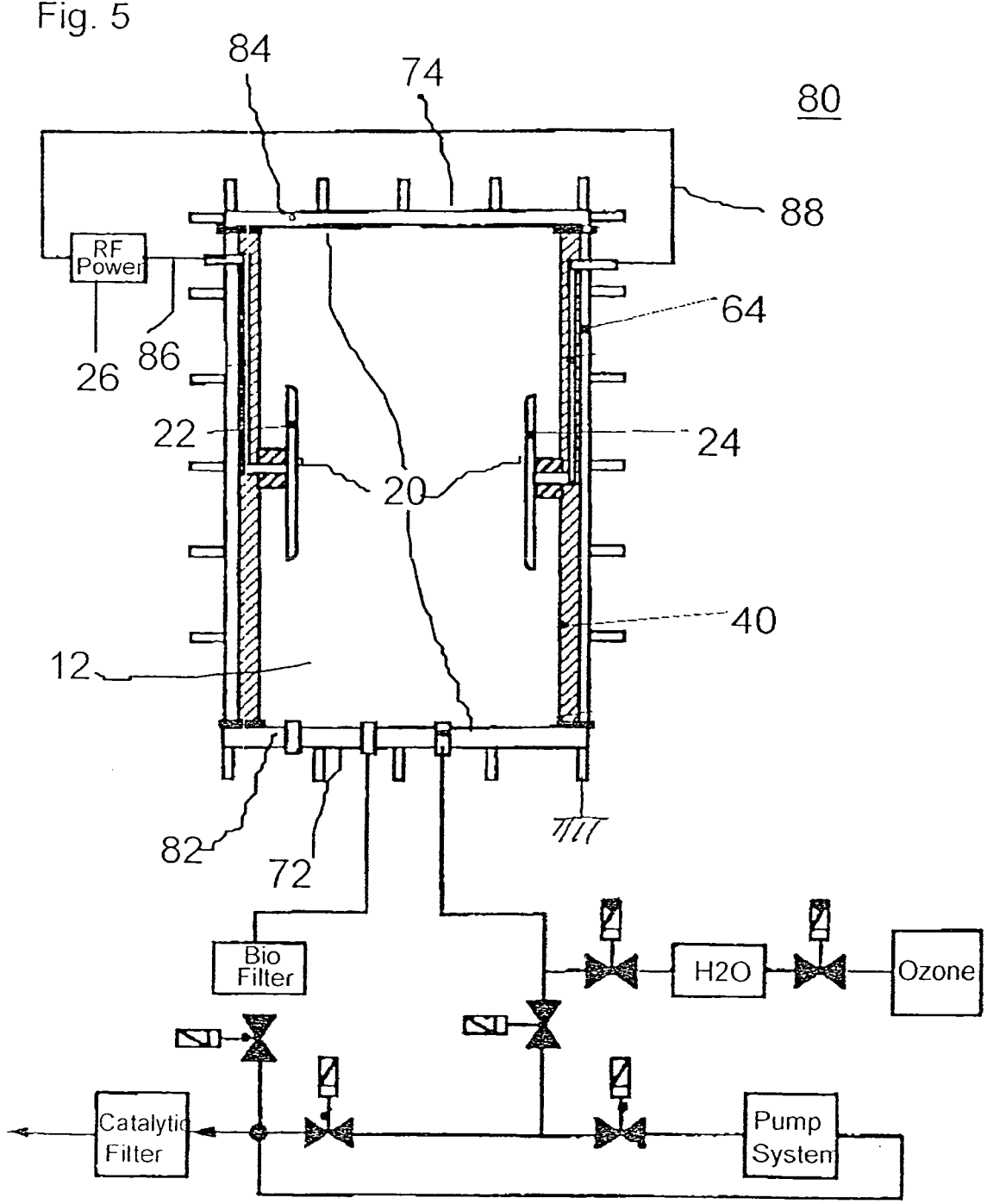
FIG. 5 is a schematic diagram of an ozone-plasma sterilization system that is constructed and operable in accordance with a second alternate embodiment of the present invention.

Reference is now made to FIG. 5, which is a schematic diagram of an ozone-plasma sterilization system 80 that is constructed and operable in accordance with a second alternate embodiment of the present invention. Ozone-plasma sterilization system 80 is the same as ozone-plasma sterilization system 70 (FIG. 4) except for the following differences. Electrode 24 is implemented as a standalone electrode. Electrode 22 is electrically connected to one of the outlets of electrical supply system 26 via a wire 86 and electrode 24 is electrically connected to the other outlet of electrical supply system 26 via a wire 88. Electrode arrangement 20 also includes another two electrodes 82, 84. Electrode 82 is implemented as part of door 72 and electrode 84 is implemented as part of door 74. Electrode 82 and electrode 84 are grounded. The surfaces of walls 64 facing into chamber 12 are covered by insulating layer 40.

Figure 6:
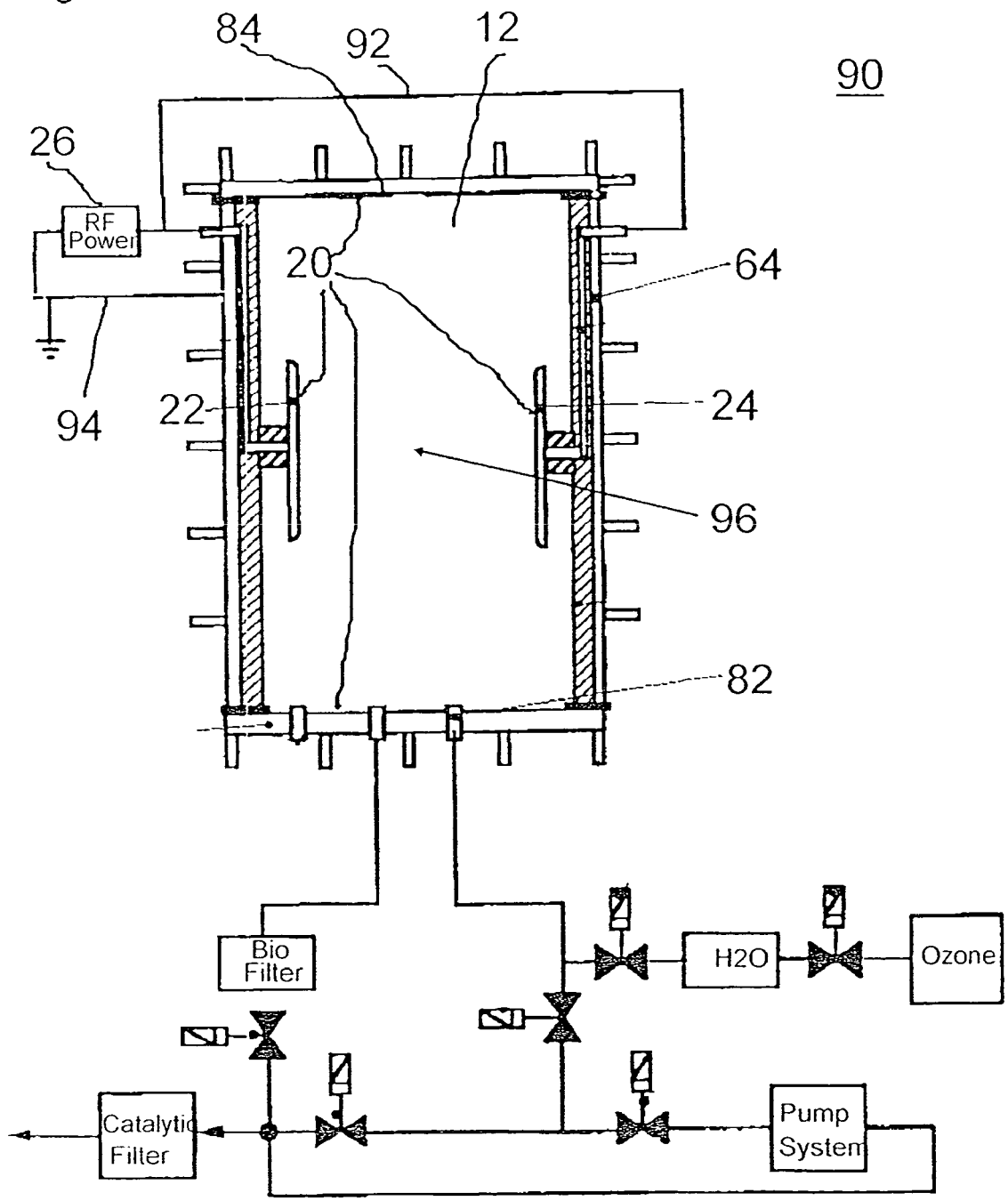
FIG. 6 is a schematic diagram of an ozone-plasma sterilization system that is constructed and operable in accordance with a third alternate embodiment of the present invention.

Reference is now made to FIG. 6, which is a schematic diagram of an ozone-plasma sterilization system 90 that is constructed and operable in accordance with a third alternate embodiment of the present invention. Ozone-plasma sterilization system 90 is the same as ozone-plasma sterilization system 80 (FIG. 5) except for the following differences. Electrode 22 and electrode 24 are electrically connected to the same outlet of electrical supply system 26 via a wire 92. The other outlet of electrical supply system 26 is grounded and is electrically connected to electrode 82, electrode 84 via a wire 94. Therefore, electrode arrangement 20 and electrical supply system 26 are configured, such that when electrical supply system 26 is actuated there is one central region 96 of zero field gradient within chamber 12. Central region 96 is defined herein to include a region which does not extend to walls 64 of chamber 12. Therefore, medical equipment or parts thereof which may be damaged by the electrical discharge are disposed within central region 96 of chamber 12. It will be apparent to those ordinarily skilled in the art that electrode arrangement 20 and electrical supply system 26 can be configured, such that when electrical supply system 26 is actuated there is more than one central region of zero field gradient within chamber 12.

Figure 7:
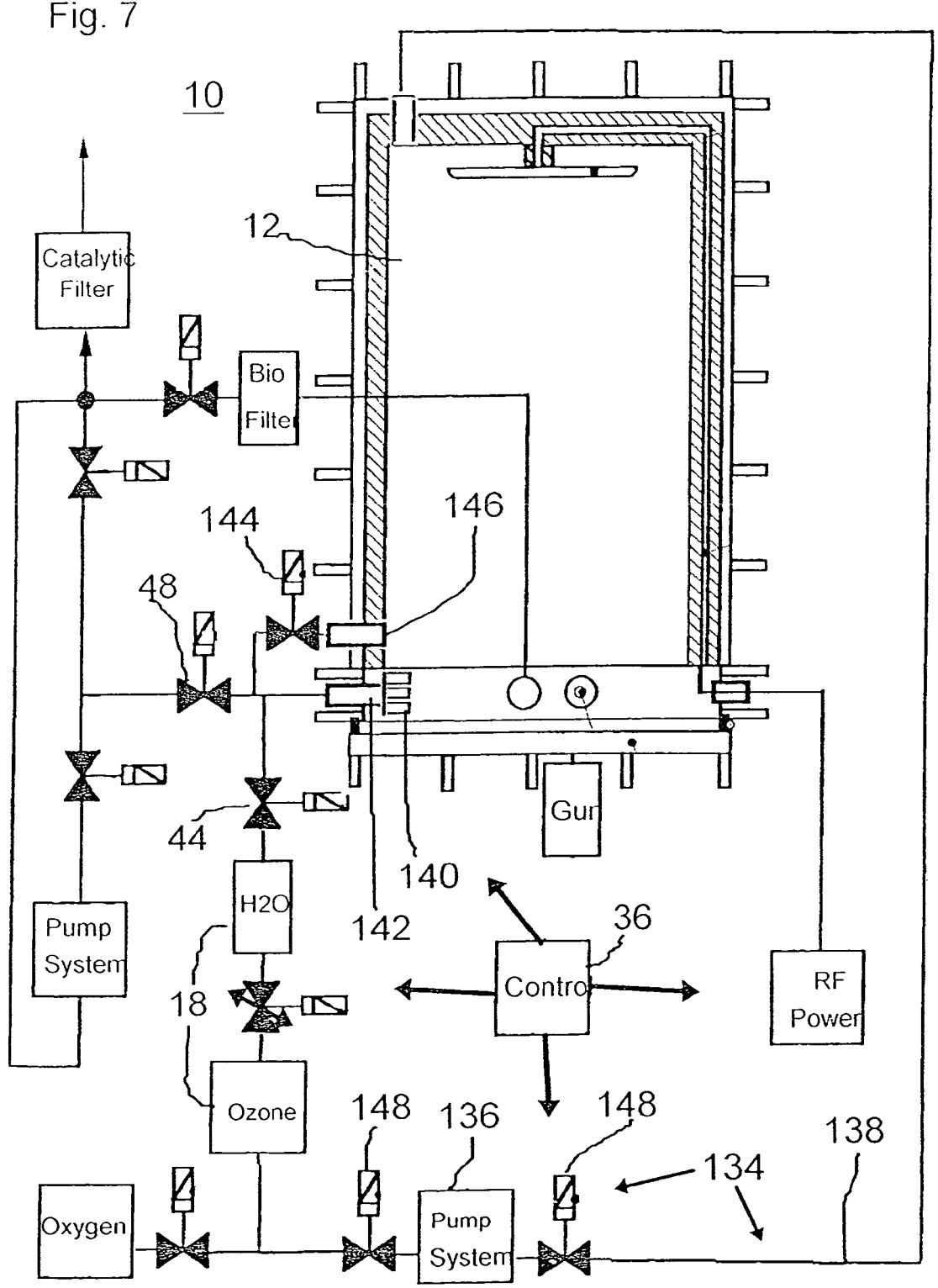
FIG. 7 is a schematic diagram of an ozone recycling system for use with the sterilization system of FIG. 1.

Reference is now made to FIG. 7, which is a schematic diagram of an ozone recycling system 134 for use with sterilization system 10 of FIG. 1. Ozone recycling system 134 includes a pumping system 136, a tubing arrangement 138, and two valves 148. Ozone recycling system 134 is configured for recycling of ozone in chamber 12 as follows. Valves 148 are opened by control system 36. Then, ozone and water vapor is pumped by pumping system 136 around a circuit including ozone and water vapor system 18, chamber 12 and tubing arrangement 138. Ozone recycling is, optionally, either performed each cycle after the electrical discharge has been broken or as a stand-alone sterilization process. In accordance with a most preferred embodiment of the present invention, ozone-recycling system 134 includes a connector arrangement 140. Connector arrangement 140 is a simple tube or a manifold having multiple outlets. Connector arrangement 140 is connected to an inlet 142 of chamber 12. One or more of the items for sterilization are mechanically connected to connector arrangement 140 within chamber 12. Ozone and water vapor is then recycled via the internal volume of the items for sterilization via connector arrangement 140 so as to contribute to sterilization of the items for sterilization. The term "internal volume" is defined as the volume created by disposing planar seals over the openings of an item for sterilization. A valve 144 is disposed between valve 48, valve 44 and an inlet 146 to chamber 12. Inlet 146 is the main inlet for ozone and water vapor into chamber 12. Inlet 146 is used when ozone and water vapor is added to chamber 12 when the electrical discharge is generated. However, when connector arrangement 140 is in use, valve 144 is closed to ensure that ozone and water vapor is recycled via connector arrangement 140 and not inlet 146.

Figure 8:
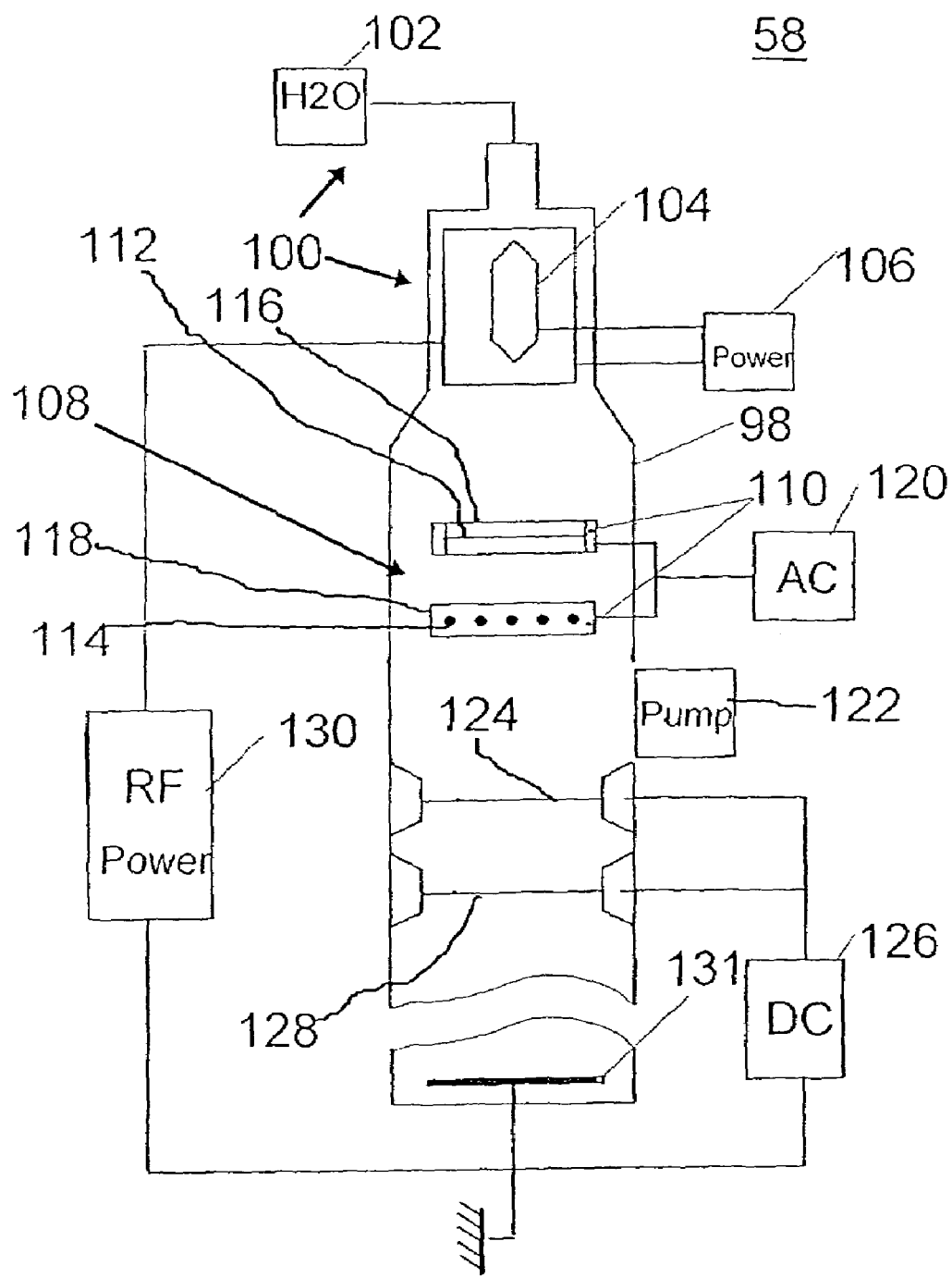
FIG. 8 is a schematic diagram of a plasma gun for use with the sterilization system of FIG. 1.

Reference is now made to FIG. 8, which is a schematic diagram of plasma gun 58 for use with sterilization system 10 of FIG. 1. Plasma gun 58 is configured to produce OH radicals. However, it will be apparent to those ordinarily skilled in the art that plasma gun 58 can be modified to produce other radicals. Plasma gun 58 includes a housing 98 and a supply system 100 which is associated with housing 98. Housing 98 is formed from a material which withstands temperatures in the range of 600 degrees centigrade to 1000 degrees centigrade and plasma discharge conditions, for example, but not limited to, quartz, ceramic, Pyrex, electronic glass and metal ceramic. Supply system 100 includes a water vapor supply 102 configured to produce water vapor in supply system 100. Supply system 100 also includes an electrode arrangement 104 disposed in supply system 100. Electrode arrangement 104 is typically formed from materials used for the electrodes of electron tubes. Supply system 100 also includes a power supply 106 electrically connected to electrode arrangement 104. Power supply 106 and electrode arrangement 104 are configured for generating electrical discharge in supply system 100, such that the electrical discharge produces negative and positive ions, including OH ions from the water vapor. Power supply 106 is typically an AC power supply with a voltage output of up to 450 volts and a power output of 100 watts and a frequency of between 50 hertz and 20 kilohertz.

Plasma gun 58 includes a dispersing arrangement 108 which is configured to disperse the positive and negative ions in order to reduce recombination of the positive and negative ions. Dispersing arrangement 108 includes a conducting arrangement 110 having two cross-aligned grills 112, 114. Dispersing arrangement 108 includes two insulation layers 116, 118 configured to insulate grill 112 and grill 114, respectively, such that conducting arrangement 110 is electrically insulated from the positive and negative ions. Insulation layer 116 and insulation layer 118 are typically formed from an insulating material which withstands temperatures in the range of 600 degrees centigrade to 1000 degrees centigrade and plasma discharge conditions, for example, but not limited to, quartz, ceramic, Pyrex and electronic glass. Dispersing arrangement 108 includes an alternating power supply 120, typically having a voltage output of 10 kilovolts, a power output of up to 500 watts and a frequency in the range of 50 hertz to 20 kilohertz. One outlet of alternating power supply 120 is electrically connected to grill 112 and the other outlet of alternating power supply 120 is electrically connected to grill 114. Grill 112 and grill 114 each include substantially parallel conducting rods. The conducting rods generally have a length of between 30 and 200 mm and a diameter of 1 mm. The conducting rods are generally spaced with a gap of 1 to 2 mm. The rods of grill 112 are cross-aligned with the rods of grill 114, such that the angle between the direction of elongation of the rods of grill 112 and the direction of elongation of the rods of grill 114 is greater than 45 degrees, preferably 90 degrees.

Plasma gun 58 also includes a vacuum pump 122 associated with housing 98. By way of example, vacuum pump 122 typically has a pumping rate of approximately 100 liters per minute when the volume of housing 98 is 1 liter. Plasma gun 58 also includes a charged arrangement 124 including a mesh. The mesh is formed from a material which withstands the conditions within housing 98, particularly chemical corrosion from the OH radicals. The mesh is formed from, by way of example, but not limited to, a gold plated conductor. Charged arrangement 124 is configured for being positively charged by connection to a DC power supply 126. Power supply 126 typically has a voltage output of up to 1,000 volts and a power output of up to 100 Watts. Charged arrangement 124 is configured for repelling the positive ions, such that at least 50% of the positive ions are removed from housing 98 via vacuum pump 122. Charged arrangement 124 is also configured for neutralizing negative ions, thereby producing radicals from the negative ions. It will be appreciated by those skilled in the art that charged arrangement 124 can be negatively charged to produce radicals from positive ions. Plasma gun 58 also includes a charged arrangement 128 including a mesh. Charged arrangement 128 is configured for being negatively charged by connection to power supply 126. Charged arrangement 128 is configured for repelling any remaining negative ions, such that at least 50% of the remaining negative ions are removed from housing 98 via vacuum pump 122. Plasma gun 58 includes a main power supply 130 which is electrically connected to power supply 106 and power supply 126. Power supply 130 is preferably an RF power supply having a DC balance. Power supply 130 typically has a voltage output of 400 volts to 2 kilovolts and a power output up to 100 kilowatts. There is a grounded plate 131 disposed within housing 98 at the opposite end to electrode arrangement 104.

Figure 9:
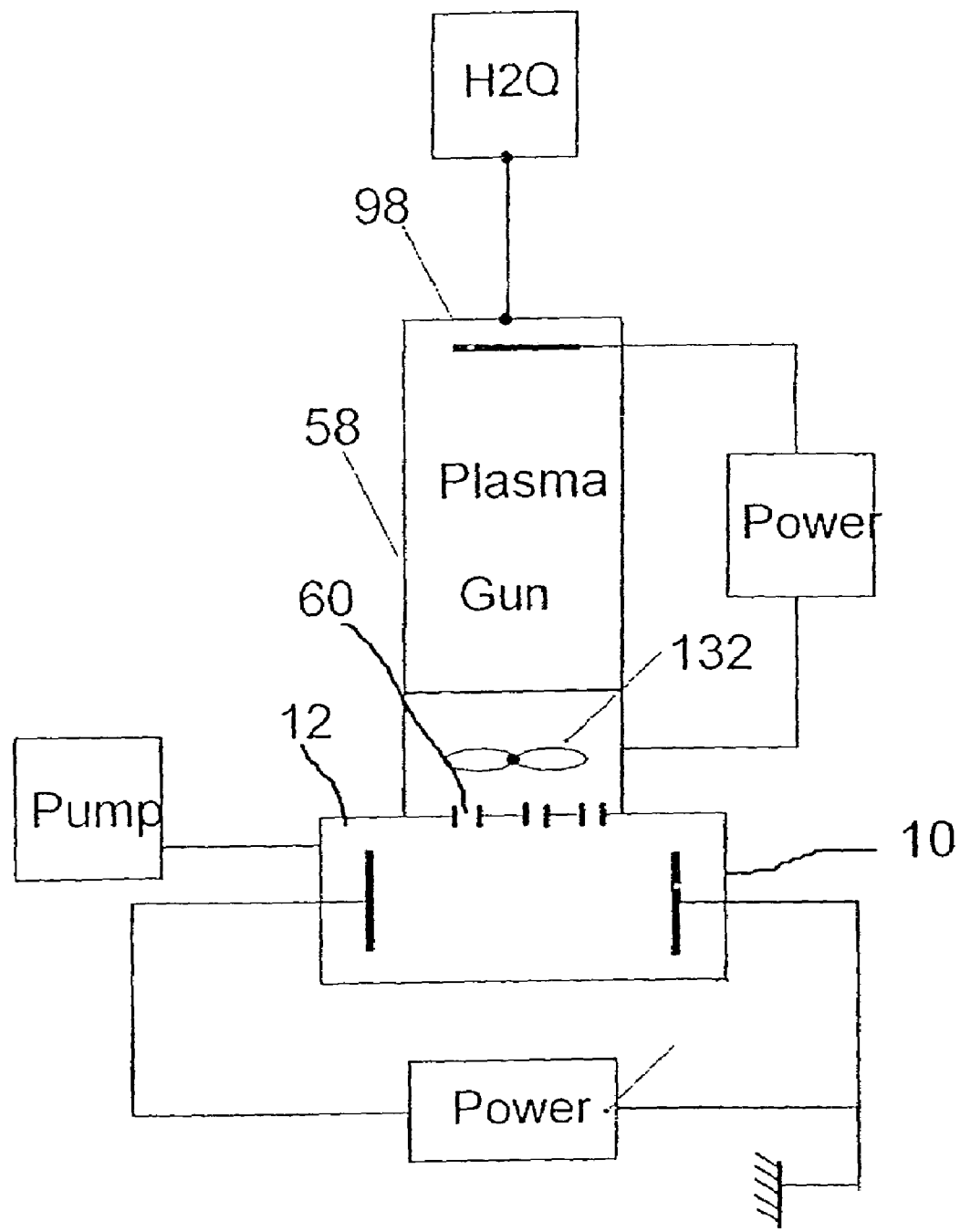
FIG. 9 is a schematic diagram of the plasma gun of FIG. 8 operationally connected to the sterilization system of FIG. 1.

Reference is now made to FIG. 9, which is a schematic diagram of plasma gun 58 of FIG. 8 operationally connected to sterilization system 10 of FIG. 1. Plasma gun 58 includes a dry vacuum pump 132, for example, but not limited to, a scroll pump, configured for pumping the OH radicals from housing 98 into chamber 12 of sterilization system 10 via connector arrangement 60. Connector arrangement 60 is typically formed from any material that withstands chemical corrosion from OH radicals. Connector arrangement 60 is a simple tube or a manifold having multiple outlets. Connector arrangement 60 is disposed between plasma gun 58 and chamber 12. One or more of the items for sterilization are mechanically connected to connector arrangement 60 within chamber 12. Plasma gun 58 then injects OH radicals into the internal volume of the items for sterilization via connector arrangement 60 so as to contribute to sterilization of the items for sterilization. Therefore, plasma gun 58 and connector arrangement 60 perform sterilization of the internal surfaces of medical equipment, for example catheters. The term "internal volume" is defined as the volume created by disposing planar seals over the openings of an item for sterilization.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

What is claimed is:

1. A method for sterilizing at least one item in a chamber, comprising the steps of:
   (a) disposing the at least one item in the chamber; and
   (b) performing a plurality of cycles including:
      (i) pumping the atmosphere from the chamber until the atmosphere of the chamber has a pressure of less than one torr;
      (ii) generating electrical discharge in the chamber;
      (iii) adding water vapor and ozone to the chamber such that said electrical discharge produces OH radicals from said water vapor and said ozone so as to contribute to sterilization of at least part of the at least one item, said adding being performed so as to increase the pressure of the atmosphere within the chamber until the pressure reaches between 5 torr and 15 torr and said electrical discharge is broken.

2. The method of claim 1, wherein said step of pumping is performed by pumping the atmosphere from the chamber until the atmosphere of the chamber has a pressure of less than half a torr.

3. The method of claim 1, further comprising the step of producing said ozone from oxygen using an ozonizer.

4. The method of claim 1, further comprising the step of producing said water vapor by passing at least part of said ozone over a reservoir of water.

5. The method of claim 1, wherein said steps are repeated cyclically at least 20 times.

6. The method of claim 1, wherein said steps are repeated cyclically at least 60 times.

7. The method of claim 1, further comprising the step of allowing said OH radicals to diffuse in the chamber for a specified diffusion time prior to repeating said step of pumping.

8. The method of claim 1, further comprising the step of recycling at least part of said ozone which was added to the chamber.

9. The method of claim 1, further comprising the step of injecting radicals into the chamber.

10. The method of claim 9, wherein said radicals include OH radicals.

11. The method of claim 9, wherein:
   (a) the at least one item has an internal volume; and
   (b) said step of injecting is performed by injecting at least part of said radicals into said internal volume of the at least one item.

12. A system for sterilizing at least one item, comprising:
   (a) a chamber having a first door, said first door being configured, such that the at least one item is entered into said chamber via said first door;
   (b) a pumping system associated with said chamber, said pumping system being configured to pump the atmosphere from said chamber until the atmosphere of said chamber has a pressure of less than one torr;
   (c) an ozone and water vapor system associated with said chamber, said ozone and water vapor system being configured for adding ozone and water vapor to said chamber;
   (d) an electrode arrangement disposed in said chamber;
   (e) an electrical supply system electrically connected to said electrode arrangement, said electrical supply system and said electrode arrangement being configured for generating electrical discharge in said chamber; and
   (f) a control system configured for actuating said pumping system, said ozone and water vapor system and said electrical supply system, said control system being configured for performing a cycle including:
      (i) actuating said pumping system to pump the atmosphere of said chamber until the atmosphere of said chamber has a pressure of less than half a torr;
      (ii) actuating said electrical supply system to generate said electrical discharge in said chamber;
      (iii) actuating said ozone and water vapor system to introduce said water and said ozone into said chamber such that said electrical discharge produces OH radicals from said water and said ozone so as to contribute to sterilization of at least part of the at least one item, said adding being performed so as to increase the pressure of the atmosphere within the chamber until the pressure reaches between 5 torr and 15 torr and said electrical discharge is broken.

13. The system of claim 12, wherein said pumping system is configured to pump the atmosphere from said chamber until the atmosphere of said chamber has a pressure of less than half a torr.

14. The system of claim 12, wherein said ozone and water vapor system includes an ozonizer configured to produce said ozone from oxygen.

15. The system of claim 12 wherein said ozone and water vapor system includes a reservoir configured for storing water, said ozone and water vapor system being configured to produce said water vapor by passing at least part of said ozone over said water.

16. The system of claim 12, wherein said control system is configured for performing said cycle at least 20 times.

17. The system of claim 12, wherein said control system is configured for performing said cycle at least 60 times.

18. The system of claim 12, further comprising a biological filter configured to filter air entering said chamber on completion of a sterilization process.

19. The system of claim 12, further comprising a ozone destruction filter configured to substantially prevent a part of said ozone exiting to a surrounding atmosphere when said pumping system is actuated.

20. The system of claim 12, wherein said electrode arrangement includes an electrode which is implemented as at least part of said first door.

21. The system of claim 12, further comprising a second door configured, such that the at least one item is removed from said chamber via said second door on completion of a sterilization process.

22. The system of claim 21, wherein said electrode arrangement includes a first electrode which is implemented as at least part of said second door.

23. The system of claim 22, wherein said electrode arrangement includes a second electrode which is implemented as at least part of said first door.

24. The system of claim 23, wherein:
(a) said electrode arrangement includes a third electrode and a fourth electrode; and
(b) said electrode arrangement and said electrical supply system are configured, such that when said electrical supply system is actuated there is at least one central region of zero field gradient within said chamber.

25. The system of claim 12, further comprising a secondary pumping system associated with said chamber, said secondary pumping system being configured to recycle at least part of said ozone which was added to the chamber.

26. The system of claim 12, further comprising a plasma gun configured for injecting radicals into said chamber.

27. The system of claim 26, wherein said radicals include OH radicals.

28. The system of claim 26, further comprising a connector arrangement configured, such that said plasma gun injects at least part of said radicals into an internal volume of the at least one item.

* * * * *